United States Patent [19]

Coates et al.

[11] Patent Number: 4,725,615

[45] Date of Patent: Feb. 16, 1988

[54] CARBAZOLE DERIVATIVES AND THEIR USE AS 5HT-INDUCED ANTAGONISTS

[75] Inventors: Ian H. Coates, Hertford; James A. Bell, Ware; David C. Humber, London; George B. Ewan, Chalfont St. Peter, all of England

[73] Assignee: Glaxo Group Limited

[21] Appl. No.: 888,258

[22] Filed: Jul. 23, 1986

[30] Foreign Application Priority Data

Jul. 24, 1985 [GB] United Kingdom ............... 8518743

[51] Int. Cl.⁴ ............... A61K 31/40; A61K 31/415; C07D 403/06; C07D 401/06
[52] U.S. Cl. ............... 514/397; 514/212; 514/323; 546/200; 540/602; 548/336; 548/439
[58] Field of Search ............... 548/336, 439; 540/602; 514/212, 323, 397; 546/200

[56] References Cited

U.S. PATENT DOCUMENTS

| | | | |
|---|---|---|---|
| 3,634,420 | 1/1972 | Littell et al. | 548/336 |
| 3,671,544 | 6/1972 | Meltzer et al. | 548/439 |
| 3,740,404 | 6/1982 | Littell et al. | 548/336 |
| 4,334,070 | 6/1982 | Berger et al. | 548/336 |

FOREIGN PATENT DOCUMENTS

| | | | |
|---|---|---|---|
| 0115607 | 8/1984 | European Pat. Off. | 548/336 |
| 1201061 | 8/1967 | United Kingdom | 548/336 |
| 1108578 | 4/1968 | United Kingdom | 548/336 |

OTHER PUBLICATIONS

R. Littell, E. N. Greenblatt and G. R. Allen, Jr., J. Med. Chem. 15(8) 875-6, 1972.
Evans, D. D., Aust. J. Chem, 26(11), 2555-8, 1973.
J. C. Lancelot, et al., Chem. & Pharm. Bul., 1983, 31, 2652-2661.
Y. Oikawa et al., J. Org. Chem., 1977, 42, 1213-1216.

Primary Examiner—Alan L. Rotman
Assistant Examiner—J. Richter

Attorney, Agent, or Firm—Bacon & Thomas

[57] ABSTRACT

The invention relates to compounds of the general formula (I):

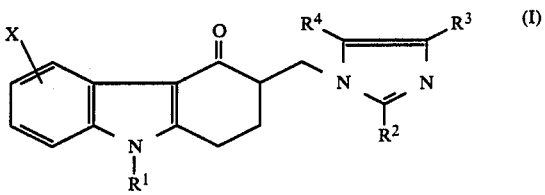

wherein
$R^1$ represents a hydrogen atom or a $C_{1-10}$ alkyl, $C_{3-7}$ cycloalkyl, $C_{3-7}$cycloalkyl-($C_{1-4}$)-alkyl, $C_{3-6}$ alkenyl, $C_{3-10}$ alkynyl, phenyl or phenyl-($C_{1-3}$)alkyl group;
one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represents a hydrogen atom or a $C_{1-6}$ alkyl group; and X represents a halogen atom or a hydroxy, $C_{1-4}$ alkoxy, phenyl-($C_{1-3}$)-alkoxy or $C_{1-6}$ alkyl group or a group $NR^5R^6$ or $CONR^5R^6$ wherein $R^5$ and $R^6$, which may be the same or different, each represents a hydrogen atom or a $C_{1-4}$ alkyl or $C_{3-4}$ alkenyl group, or together with the nitrogen atom to which they are attached form a saturated 5 to 7 membered ring; and physiologically acceptable salts and solvates thereof.

The compounds are potent and selective antagonists of "neuronal" 5-hydroxytryptamine receptors and are useful in the treatment of psychotic disorders (e.g. schizophrenia and mania;); anxiety, pain; gastric stasis; symptoms of gastrointestinal dysfunction such as occur with dyspepsia, peptic ulcer, reflux oesophagitis and flatulence; migraine; and nausea and vomiting.

13 Claims, No Drawings

CARBAZOLE DERIVATIVES AND THEIR USE AS 5HT-INDUCED ANTAGONISTS

This invention relates to heterocyclic compounds, to processes for their preparation, to pharmaceutical compositions containing them and to their medical use. In particular the invention relates to compounds which act upon 5-hydroxytryptamine (5-HT) receptors of the type located on terminals of primary afferent nerves.

According to one aspect the present invention provides a tetrahydrocarbazolone of the general formula (I):

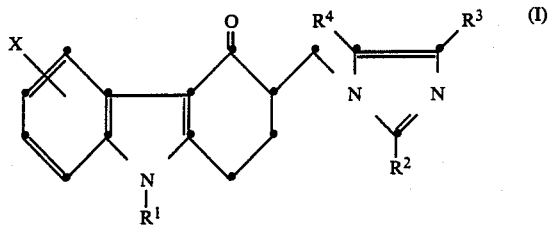

wherein
R$^1$ represents a hydrogen atom or a C$_{1-10}$ alkyl, C$_{3-7}$ cycloalkyl, C$_{3-7}$cycloalkyl-(C$_{1-4}$)-alkyl, C$_{3-6}$ alkenyl, C$_{3-10}$ alkynyl, phenyl or phenyl-(C$_{1-3}$) alkyl group;

one of the groups represented by R$^2$, R$^3$ and R$^4$ is a hydrogen atom or a C$_{1-6}$ alkyl, C$_{3-7}$ cycloalkyl, C$_{2-6}$ alkenyl or phenyl-(C$_{1-3}$)alkyl group and each of the other two groups, which may be the same or different, represents a hydrogen atom or a C$_{1-6}$ alkyl group; and X represents a halogen atom or a hydroxy, C$_{1-4}$ alkoxy, phenyl-(C$_{1-3}$)-alkoxy or C$_{1-6}$ alkyl group or a group NR$^5$R$^6$ or CONR$^5$R$^6$ wherein R$^5$ and R$^6$, which may be the same or different, each represents a hydrogen atom or a C$_{1-4}$ alkyl or C$_{3-4}$ alkenyl group, or together with the nitrogen atom to which they are attached form a saturated 5 to 7 membered ring; and physiologically acceptable salts and solvates thereof.

It will be understood that when R$^1$ represents a C$_{3-6}$ alkenyl group or a C$_{3-10}$ alkynyl group, or R$^5$ or R$^6$ represents a C$_{3-4}$ alkenyl group, the double or triple bond may not be adjacent to the nitrogen atom.

Referring to the general formula (I), the alkyl groups represented by R$_1$, R$^2$, R$^3$, R$^4$, R$^5$, R$^6$ and X may be straight chain or branched chain alkyl groups, for example, methyl, ethyl, propyl, prop-2-yl, butyl, but-2-yl, 2-methylprop-2-yl, pentyl, pent-3-yl or hexyl.

An alkenyl group may be, for example, a propenyl group.

An alkynyl group may be for example a 2-propynyl or 2-octynyl group.

A phenyl-C$_{1-3}$ alkyl group (as such or as part of a phenyl-(C$_{1-3}$)-alkoxy group) may be, for example, a benzyl, phenethyl or 3-phenylpropyl group.

A cycloalkyl group (as such or as part of a cycloalkyl-alkyl group) may be, for example, a cyclopentyl, cyclohexyl or cycloheptyl group.

When R$^1$ represents a C$_{3-7}$cycloalkyl-(C$_{1-4}$)alkyl group, the alkyl moiety may be for example a methyl, ethyl, propyl, prop-2-yl or butyl group.

When X represents a C$_{1-4}$ alkoxy group it may be, for example, a methoxy group.

When X represents a halogen atom it may be, for example a fluorine, chlorine or bromine atom.

The substituent X may be at the 5, 6, 7 or 8 position of the tetrahydrocarbazolone.

It will be appreciated that the carbon atom at the 3-position of the tetrahydrocarbazolone ring is asymmetric and may exist in the R- or S-configuration. Furthermore, depending on the nature of the substituents R$^1$, R$^2$, R$^3$ and R$^4$, centres of isomerism may occur elsewhere in the molecule. The present invention encompasses both the individual isomeric forms of the compounds of formula (I) and all mixtures, including racemic mixtures, thereof.

Suitable physiologically acceptable salts of the compounds of general formula (I) include acid addition salts formed with organic or inorganic acids for example, hydrochlorides, hydrobromides, sulphates, phosphates, citrates, fumarates and maleates. The solvates may, for example, be hydrates.

A preferred class of compounds represented by general formula (I) is that wherein R$^1$ represents a hydrogen atom or a C$_{1-10}$ alkyl, C$_{3-7}$ cycloalkyl, C$_{3-6}$ alkenyl, phenyl or phenyl-(C$_{1-3}$)alkyl group; X represents a halogen atom, or a hydroxy, C$_{1-4}$ alkoxy or C$_{1-6}$ alkyl group, or a group NR$^5$R$^6$ or CONR$^5$R$^6$, and the groups R$^2$, R$^3$, R$^4$, R$^5$ and R$^6$ are as previously defined.

Another preferred class of compounds represented by general formula (I) is that wherein X represents a halogen atom, e.g. a bromine or fluorine atom, a C$_{1-6}$ alkyl group, e.g. a methyl group; or a hydroxy group. The substituent X is preferably at the 6-position of the tetrahydrocarbazolone ring.

A further preferred class of compounds is that wherein R$^1$ represents a hydrogen atom or a C$_{1-6}$ alkyl, C$_{3-7}$ cycloalkyl or C$_{3-6}$ alkenyl group.

Another preferred class of compounds represented by the general formula (I) is that wherein one of the groups represented by R$^2$, R$^3$ and R$^4$ represents a C$_{1-3}$ alkyl, C$_{3-6}$ cycloalkyl or C$_{3-6}$ alkenyl group and each of the other two groups, which may be the same or different, represents a hydrogen atom or a C$_{1-3}$ alkyl group. Where R$^2$ represents a hydrogen atom, R$^3$ and/or R$^4$ preferably represents a C$_{1-3}$ alkyl group. When R$^2$ represents a C$_{1-3}$ alkyl group, R$^3$ and R$^4$ both preferably represents hydrogen atoms.

Particularly preferred compounds according to the invention include:
6-fluoro-1,2,3,9-tetrahydro-9-methyl-3-[(2-methyl-1H-imidazol-1-yl) methyl]-4H-carbazol-4-one;
6-bromo-1,2,3,9-tetrahydro-9-methyl-3-[(2-methyl-1H-imidazol-1-yl) methyl]-4H-carbazol-4-one;
1,2,3,9-tetrahydro-6-hydroxy-9-methyl-3-[(2-methyl-1H-imidazol-1-yl) methyl]-4H-carbazol-4-one;
1,2,3,9-tetrahydro-6-methyl-3-[(2-methyl-1H-imidazol-1-yl)methyl]-4H-carbazol-4-one, and
6-(dimethylamino)-1,2,3,9-tetrahydro-9-methyl-3-[(2-methyl-1H-imidazol-1-yl)methyl]-4H-carbazol-4-one, and their physiologically acceptable salts and solvates.

It will be appreciated that the invention extends to other physiologically acceptable equivalents of the compounds according to the invention, i.e. physiologically acceptable compounds which are converted in vivo into the parent compound of formula (I).

Compounds of the invention are potent and selective antagonists of 5HT-induced responses of the rat isolated vagus nerve preparation and thus act as potent and selective antagonists of the 'neuronal' 5-HT receptor type located on primary afferent nerves. Receptors of this type are also belived to be present in the central nervous system. 5-HT occurs widely in the neuronal pathways in the central nervous system and disturbance of these 5-HT containing pathways is known to alter behavioural syndromes such as mood, psychomotor activity, appetite and memory.

It is believed that compounds which antagonise the effect of 5HT at 5HT receptors of the type located on the terminals of primary afferent nerves will be useful in the treatment of conditions such as psychotic disorders, (e.g. schizophrenia and mania); anxiety; pain; gastric stasis; symptoms of gastrointestinal dysfunction such as occur with dyspepsia, peptic ulcer, reflux oesophagitis and flatulence; migraine; and nausea and vomiting.

Unlike existing drug treatments for these conditions the compounds of the invention, because of their high selectivity for 5-HT receptors of the type located on primary afferent nerve terminals, would not be expected to produce undesirable side effects. Thus, for example neuroleptic drugs exhibit extrapyramidal effects, such as tardive dyskinesia, and benzodiazepines may cause dependence.

According to another aspect, the invention provides a method of treatment of a human or animal subject suffering from a psychotic disorder such as schizophrenia or mania; or from anxiety; pain; gastric stasis, symptoms of gastrointestinal dysfunction such as dyspepsia, reflux oesophagitis, peptic ulcer or flatulence; migraine; nausea or vomiting, which comprises administering an effective amount of a compound of formula (I) or a physiologically acceptable salt or solvate thereof.

Accordingly, the invention also provides a pharmaceutical composition which comprises at least one compound selected from 3-imidazolylmethyltetrahydrocarbazolone derivatives of the general formula (I), and their physiologically acceptable salts and solvates, e.g. hydrates, adapted for use in human or veterinary medicine, and formulated for administration by any convenient route.

Such compositions may be formulated in conventional manner using one or more physiologically acceptable carriers or excipients.

Thus the compounds of the invention may be formulated for oral, buccal, parenteral, topical or rectal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by injection. Formulations for injection may be presented in unit dosage from e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in power from for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for administration to man (of approximately 70 kg body weight) is 0.05 to 20 mg, preferably 0.1 to 10 mg of the active ingredient per unit dose which could be administered, for example, 1 to 4 times per day. The dose will depend on the route of administration and the body weight of the patient. It will be appreciated that it may be necessary to make routine variations to the dosage depending on the age and weight of the patient as well as the severity of the condition to be treated.

For oral administration a unit dose will preferably contain from 0.5 to 10 mg of the active ingredient. A unit dose for parenteral administration will preferably contain 0.1 to 10 mg of the active ingredient.

Aerosol formulations are preferably arranged so that each metered dose or 'puff' delivered from a pressurised aerosol contains 0.2 mg to 2 mg, of a compound of the invention, and each dose administered via capsules and cartridges in an insufflator or an inhaler contains 0.2 to 20 mg of a compound of the invention. The overall daily dose by inhalation will be within the range 0.4 to 80 mg. Administration may be several times daily, for example from 2 to 8 times, giving for example 1, 2 or 3 doses each time.

The compounds of the invention may, if desired, be administered in combination with one or more other therapeutic agents, such as cytostatic agents, e.g. cisplatin or cyclophosphamide.

According to another aspect of the invention, compounds of general formula (I) and physiologically acceptable salts or solvates or physiologically acceptable equivalents thereof may be prepared by the general methods outlined hereinafter.

According to a first general process (A), a compound of general formula (I) or a physiologically acceptable salt or solvate or a physiologically acceptable equivalent thereof may be prepared by reacting a compound of general formula (II):

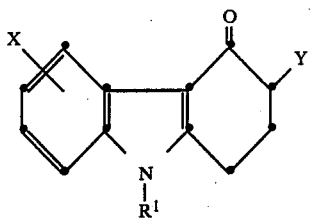

(wherein $R^1$ and X are as defined previously and Y represents a reactive substituent) or a protected derivative thereof with an imidazole of general formula (III):

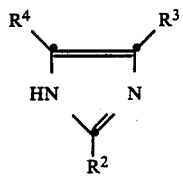

(wherein $R^2$, $R^3$ and $R^4$ are as defined previously) or a salt thereof.

Examples of compounds of formula (II) which may be employed as starting materials in the process (A) include compounds wherein Y represents a group selected from an alkenyl group $=CH_2$ or a group of formula $CH_2Z$ where Z represents a leaving atom or group, such as a halogen atom, e.g. chlorine or bromine; an acyloxy group such as acetoxy, trifluoromethanesulphonyloxy, p-toluene sulphonyloxy or methanesulphonyloxy; a group $—N^+R^7R^8R^9E^-$, (where $R^7$, $R^8$ and $R^9$ each independently represents lower alkyl e.g. methyl, aryl e.g. phenyl, or aralkyl e.g. benzyl and $E^-$ represents an anion such as a halide ion, e.g. chloride, bromide or iodide); or a group $—NR^7R^8$, where $R^7$ and $R^8$ are as previously defined, for example $—N(CH_3)_2$.

When Y represents the group $=CH_2$, the process may conveniently be carried out in a suitable solvent, examples of which include water; esters, e.g. ethyl acetate; ketones, e.g. acetone or methylisobutylketone; amides, e.g. dimethylformamide; alcohols, e.g. ethanol; and ethers e.g. dioxan or tetrahydrofuran; or mixtures thereof. The process may be effected at a temperature of, for example, 20° to 100° C.

When Y represents the group $CH_2Z$, where Z is a halogen atom or an acyloxy group, the process may conveniently be carried out in a suitable solvent such as an amide, e.g. dimethylformamide; an alcohol, e.g. methanol or industrial methylated spirit; or a haloalkane, e.g. dichloromethane, and at a temperature of from $-10°$ to $+150°$ C., e.g. $+20°$ to $+100°$ C.

The reaction of a compound of formula (II) where Y represents the group $CH_2Z$ where Z is the group $—N^+R^7R^8R^9E^-$, may conveniently be carried out in a suitable solvent such as water, an amide, e.g. dimethylformamide; a ketone, e.g. acetone; or an ether, e.g. dioxan, and at a temperature of from 20° to 150° C.

The reaction of a compound of formula (II) where Y represents the group $—CH_2Z$, where Z is the group $—NR^7R^8$, may conveniently be carried out in a suitable solvent such as water; an alcohol e.g. methanol; or an amide e.g. dimethylformamide, or mixtures thereof, and at a temperature of from 20° to 150° C.

The compounds of formula (II) are novel compounds and form a further feature of the invention.

The starting materials of formula (II) wherein Y represents the group $=CH_2$ may be prepared from compounds of formula (II) where Y represents the group $—CH_2N^+R^7R^8R^9E^-$ by reaction with a base in a suitable solvent. Examples of bases which may be employed include alkali metal hydroxides, e.g. potassium hydroxide, alkali metal carbonates or hydrogen carbonates e.g. sodium hydrogen carbonate, and tertiary amines, e.g. diisopropylethylamine.

The quaternary salts may be formed from the corresponding tertiary amine by reaction with an alkylating agent such as methyl iodide or dimethyl sulphate, if preferred in a suitable solvent, e.g. dimethylformamide. The tertiary amine (i.e. wherein Y represents a group $—CH_2NR^7R^8$) may be prepared by reaction of a tetrahydrocarbazolone of general formula (IV):

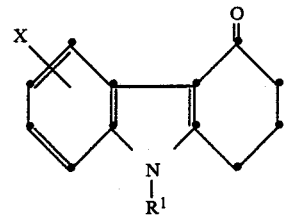

(wherein $R^1$ and X are as defined previously) with formaldehyde and the corresponding secondary amine, if desired in a suitable solvent such as an alcohol, e.g. ethanol, or an organic acid e.g. acetic acid.

Compounds of general formula (IV) may be prepared for example, according to the method of processes (B), (D) or (E) as described hereinafter using the appropriate starting materials.

The starting materials of general formula (II) where Y represents $—CH_2Z$ where Z is a halogen atom or an acyloxy group may be prepared from the corresponding hydroxymethyl derivative of general formula (V):

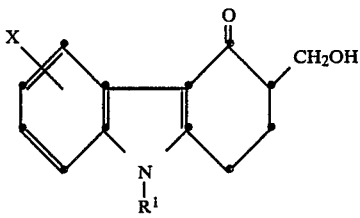

(wherein $R^1$ and X are as defined previously)
which itself may be obtained by reacting the tetrahydrocarbazolone of general formula (IV) with formaldehyde, preferably in a suitable solvent such as an alcohol, e.g. ethanol, and preferably in the presence of a base.

Thus, the compounds where Z is a halogen atom may be obtained by reacting a compound of formula (V) with a halogenating agent such as a phosphorus trihalide, e.g. phosphorus trichloride.

The compounds where Z is an acyloxy group may be prepared by reacting a compound of formula (V) with an appropriate acylating agent such as an anhydride or a sulphonyl halide such as a sulphonyl chloride, optionally in the presence of a base e.g. triethylamine or pyridine.

Compounds of formula (II) where Y represents —$CH_2Z$ where Z is a halogen atom may also be prepared by reacting a compound of formula (II) where Y represents the group =$CH_2$ with the appropriate hydrogen halide, e.g. hydrogen chloride, conveniently in a suitable solvent such as an ether, e.g. diethyl ether.

According to another general process (B) a compound of formula (I) may be prepared by oxidising a compound of formula (VI):

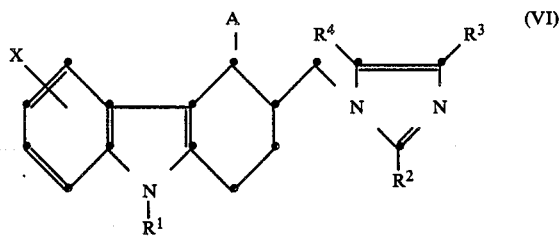

(wherein A represents a hydrogen atom or a hydroxyl group and $R^1$, $R^2$, $R^3$, $R^4$ and X are as previously defined) or a salt or a protected derivative thereof.

The oxidation process may be effected using conventional methods and the reagents and reaction conditions should be chosen such that they do not cause oxidation of other part of the molecule. Thus, the oxidation process is preferably effected using a mild oxidising agent.

When oxidising a compound of formula (VI) in which A represents a hydrogen atom, suitable oxidising agents include quinones in the presence of water, e.g. 2,3-dichloro-5,6-dicyano-1,4-benzoquinone or 2,3,5,6-tetrachloro-1,4-benzoquinone; selenium dioxide; a cerium (IV) oxidising reagent such as ceric ammonium nitrate or a chromium (VI) oxidising agent, e.g. a solution of chromic acid in acetone (for example Jones' reagent) or chromium trioxide in pyridine.

When oxidising a compound of formula (VI) in which A represents a hydroxyl group, suitable oxidising agents include quinones in the presence of water, e.g. 2,3-dichloro-5,6-dicyano-1,4-benzoquinone or 2,3,5,6-tetrachloro-1,4-benzoquinone; ketones, e.g. acetone methylethylketone or cyclohexanone, in the presence of a base e.g. aluminium t-butoxide; a chromium (VI) oxidising agent, e.g. a solution of chromic acid in acetone (for example Jones reagent) or chromium trioxide in pyridine; an N-halosuccinimide, e.g. N-chlorosuccinimide or N-bromosuccinimide; a dialkylsulphoxide e.g. dimethylsulphoxide, in the presence of an activating agent such as N,N'- dicyclohexylcarbodiimide or an acyl halide, e.g. oxalyl chloride or tosyl chloride; pyridine-sulphur trioxide complex; or a dehydrogenation catalyst such as copper chromite, zinc oxide, copper or silver.

Suitable solvents may be selected from ketones, e.g. acetone or butanone; ethers e.g. tetrahydrofuran or dioxan; amides, e.g. dimethylformamide; hydrocarbons, e.g. benzene or toluene; halogenated hydrocarbons, e.g. dichloromethane; and water or mixtures thereof.

The process may be conveniently effected at a temperature of $-70°$ to $+50°$ C. It will be understood that the preferred reaction temperature will depend inter alia on the choice of oxidising agent.

Compounds of general formula (VI) may be prepared by reacting a compound of formula (VII):

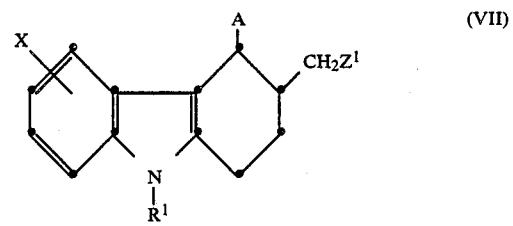

(wherein $R^1$, X and A are as defined previously and $Z^1$ is a leaving atom or group such as a halogen atom, an acyloxy group or the group —$N^+R^7R^8R^9E^-$ as previously defined for Z) with an imidazole of formula (III) according to the method of process (A) described herein.

Compounds of general formula (VI) are novel compounds and form a further feature of this invention.

Compounds of formula (VII) may be prepared by reducing compounds of formula (II) using for example lithium aluminum hydride or sodium borohydride.

Compounds of formula (VII) wherein A represents a hydrogen atom may also be prepared by reacting a compound of formula (VII) wherein A represents a hydroxyl group with a tosyl halide (e.g. tosyl chloride) and then reducing the resulting tosylate with lithium aluminium hydride.

According to another general process (C), a compound of formula (I) according to the invention or a salt or protected derivative thereof may be converted into another compound of formula (I) using conventional techniques. Such conventional techniques include alkylation, which may be effected for example in a compound of formula (I) wherein $R^1$ represents a hydrogen atom or X represents a hydroxyl group or a group $NR^5R^6$ where at least one of $R^5$ or $R^6$ represents a hydrogen atom; hydrogenation, which may, for example, be used to convert an alkenyl substituent into an alkyl substituent or a benzyloxy substituent into a hydroxyl group; and acid catalysed cleavage to convert a compound wherein X represents an alkoxy or benzyloxy group into a corresponding hydroxy-substituted compound.

The term "alkylation" includes the introduction of other groups such as cycloalkyl or alkenyl groups. Thus, for example, a compound of formula (I) in which $R^1$ represents a hydrogen atom may be converted into the corresponding compound in which $R^1$ represents a $C_{1-10}$ alkyl, $C_{3-7}$ cycloalkyl, $C_{3-7}$ cycloalkyl-$(C_{1-4})$alkyl, $C_{3-10}$ alkynyl, $C_{3-6}$ alkenyl or phenyl-$(C_{1-3})$alkyl group.

The above alkylation reaction may be effected using the appropriate alkylating agent selected from compounds of formula $R^aZ^a$ where $R^a$ represents a $C_{1-10}$alkyl, $C_{3-7}$ cycloalkyl, $C_{3-7}$-cycloalkyl-$(C_{1-4})$alkyl, $C_{3-10}$ alkynyl, $C_{3-6}$ alkenyl or phenyl-$(C_{1-3})$-alkyl group, and $Z^a$ represents a leaving group such as a halide or an acyloxy group as previously defined for Z, or a sulphate of formula $(R^a)_2SO_4$.

The alkylation reaction may conveniently be carried out in an inert organic solvent such as an amide, e.g. dimethylformamide; an ether, e.g. tetrahydrofuran; a ketone e.g. acetone; or an aromatic hydrocarbon, e.g. toluene, preferably in the presence of a base. Suitable bases include, for example, alkali metal hydrides such as sodium hydride, alkali metal amides such as sodium amide, alkali metal carbonates such as sodium carbonate or alkali metal alkoxides such as sodium or potassium methoxide, ethoxide or t-butoxide. The reaction may conveniently be effected at a temperature in the range $-20°$ to $+100°$ C., preferably $0°$ to $50°$ C.

Hydrogenation according to general process (C) may be effected using conventional procedures, for example by using hydrogen in the presence of a noble metal catalyst e.g. palladium, palladium oxide, Raney nickel, platinum, platinum oxide or rhodium. The catalyst may be supported on for example charcoal, or a homogenous catalyst such tris(triphenylphosphine) rhodium chloride may be used. The hydrogenation will generally be effected in a solvent such as an alcohol, e.g. ethanol; an amide, e.g. dimethylformamide; an ether, e.g. dioxan; or an ester, e.g. ethyl acetate, and at a temperature in the range $-20°$ to $100°$ C., preferably $0°$ to $50°$ C.

Acid catalysed cleavage according to general process (C) may be effected using a Lewis acid such as boron tribromide or aluminium trichloride. The reaction may be effected in a solvent such as a halogenated hydrocarbon e.g. dichloromethane. The reaction temperature may conveniently be in the range $-70°$ to $+100°$ C.

According to another general process (D), a compound of formula (I) may be prepared by cyclising a compound of formula (VIII):

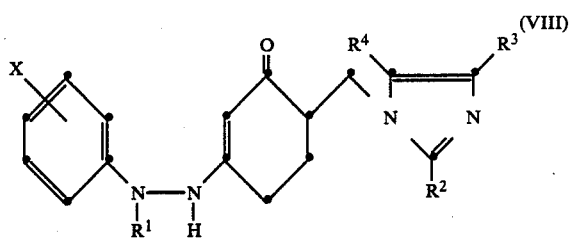

(VIII)

(wherein $R^1$, $R^2$, $R^3$, $R^4$ and X are as defined previously) or a salt or a protected derivative thereof.

It will be appreciated that the compounds of formula (VIII) may exist in the corresponding enol hydrazone tautomeric form.

The cyclisation may be carried out in aqueous or non-aqueous media, in the presence of an acid catalyst. When an aqueous medium is employed this may be water or an aqueous organic solvent such as an aqueous alcohol (e.g. methanol, ethanol or isopropanol) or an aqueous ether (e.g. dioxan or tetrahydrofuran) as well as mixtures of such solvents and the acid catalyst may be, for example, an inorganic acid such as concentrated hydrochloric or sulphuric acid. (In some cases the acid catalyst may also act as the reaction solvent). In an anhydrous reaction medium, which may comprise one or more alcohols or ethers (e.g. as described above), carboxylic acids (e.g. acetic acid) or esters (e.g. ethyl acetate), the acid catalyst will generally be a Lewis acid such as boron trifluoride, zinc chloride or magnesium chloride. The cyclisation reaction may conveniently be carried out at temperatures of from $20°$ to $200°$ C. preferably $50°$ to $125°$ C.

Alternatively the process may be carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

According to a particular embodiment of this process, compounds of general formula (I) may be prepared directly by the reaction of a compound of formula (IX)

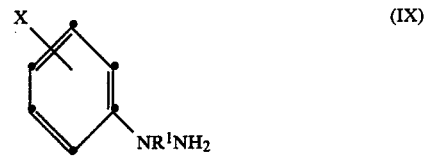

(IX)

(wherein $R^1$ and X are as defined previously) or a salt thereof with a compound of formula (X)

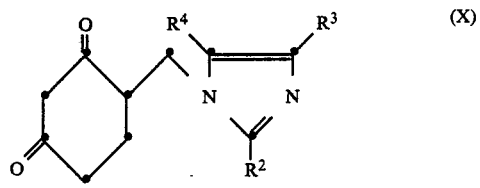

(X)

(wherein $R^2$, $R^3$ and $R^4$ are as defined previously) or a protected derivative thereof using the appropriate conditions as described above.

Compounds of general formula (VIII) may be isolated as intermediate during the process for the preparation of compounds of general formula (I) wherein a compound of formula (IX), or a salt thereof, is reacted with a compound of formula (X) or a protected derivative thereof, in a suitable solvent such as an aqueous alcohol (e.g. methanol) and at a temperature of, for example, from $20°$ to $100°$ C.

A protected derivative of general formula (X) may for example have one or both of the carbonyl groups protected e.g. as an enol ether. It will be appreciated that when a compound of formula (X) is used in which the carbonyl group at the 3-position is protected, it may be necessary to remove the protecting group in order for reaction to occur with the compound of formula (IX). Deprotection may be carried out by conventional methods, as described hereinafter. If desired, deprotection may be effected in situ.

The compounds of formula (X) may be prepared by reacting an imidazole of formula (III) with a compound of formula (XI)

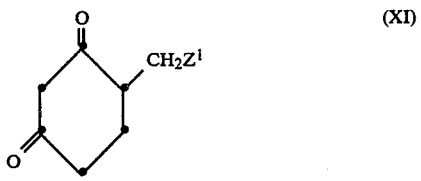

(wherein $Z^1$ is a readily displaceable atom or group such as a halogen atom, an acyloxy group or the group $-N^+R^7R^8R^9F^-$ as previously defined for (Z) or a protected derivative thereof, according to the method of process (A) described herein.

The compounds of formula (XI) may be prepared by analogous methods to those described herein for the preparation of compounds of formula (II) from compounds of formula (IV). For example, the compounds of formula (XI) wherein Z represents the group $N^+(CH_3)_3I^-$ may be prepared by a Mannich reaction using a cyclohexane-1,5-dione derivative in which one of the carbonyl groups is protected (for example as the methyl enol ether) followed by methylation. Thus the protected dione may be reacted with formaldehyde and dimethylamine, or more conveniently, the enolate may be reacted with Eschenmoser's salt $[CH_2=N^+(CH_3)_2I^-]$, followed by a methylating agent such as methyl iodide.

According to another general process (E) a compound of formula (I) may be prepared by cyclising a compound of formula (XII).

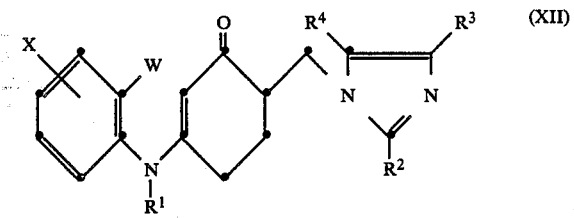

(wherein W represents a hydrogen atom or a halogen atom and $R^1$, $R^2$, $R^3$, $R^4$ and X are as defined previously) or a salt or protected derivative thereof.

When W represents a halogen atom it may be, for example, a chlorine atom or, preferably, a bromine or iodine atom.

The reaction may be effected in the presence of a palladium reagent, or, when W represents a halogen atom, in the presence of a copper (I) salt or photochemically.

The palladium reagent may be, for example, a palladium salt derived from an organic acid, e.g. an acetate, or derived from an inorganic acid, e.g. a chloride or bromide, a palladium complex such as a triarylphosphine palladium complex, e.g. a triphenylphosphine or tri(2-methylphenyl)phosphine palladium complex, or finely divided palladium metal such as palladium on charcoal. The triarylphosphine palladium complex may be generated in situ by reacting a palladium salt, e.g. palladium acetate, with the appropriate triarylphosphine.

When a palladium reagent is used in the above process, the reaction may be effected in the presence or absence of a solvent. Suitable solvents include nitriles, e.g. acetonitrile; alcohols e.g. methanol or ethanol; amides e.g. dimethylformamide, N-methylpyrrolidone or hexamethylphosphoramide; and water. The reaction may conveniently be carried out at a temperature of from 25° to 200° C., preferably 50° to 160° C.

When a compound of formula (XII) in which W represents a halogen atom is used, the palladium reagent is preferably used in the presence of a base. Only a catalytic quantity of the reagent will then be required. Suitable bases include tertiary amines e.g. triethylamine or tri-n-butylamine; and alkali metal carbonates, bicarbonates or acetates, e.g. sodium or potassium carbonate, bicarbonate or acetate.

When a compound of formula (XII) in which W represents a halogen atom other than an iodine atom, e.g. a chlorine or bromine atom is used, the palladium reagent, which may be generated in situ, is preferably a triarylphosphine palladium complex.

When a compound of formula (XII) in which W represents a hydrogen atom is used, the palladium reagent is preferably a palladium salt. The reaction may conveniently be effected in the presence of an oxidising agent such as a copper (II) or silver salt e.g. cupric acetate or silver acetate in the presence of oxygen. Only a catalytic quantity of the palladium reagent will then be required.

A compound of general formula (XII) wherein W represents a halogen atom may be cyclised according to general process (E) in the presence of a copper (I) salt, for example, copper (I) iodide. The reaction may be effected in the presence of a strong base, e.g. an alkali metal hydride such as sodium hydride or an alkali metal alkoxide such as sodium ethoxide. Suitable solvents include amides, e.g. dimethylformamide, N-methylpyrrolidone or hexamethylphosphoramide; nitriles, e.g. acetonitrile; and alcohols, e.g. ethanol. The reaction may conveniently be effected at a temperature of 50° to 200° C., preferably 100° to 170° C.

When W represents a halogen atom Process (E) may also be effected photochemically, conveniently by irradiating for example with a mercury lamp preferably a high pressure mercury lamp. Suitable solvents for the reaction include nitriles, e.g. acetonitrile; chlorinated hydrocarbons e.g. carbon tetrachloride; and cyclic ethers, e.g. tetrahydrofuran or dioxan. The reaction may conveniently be effected in the presence of a base such as a tertiary amine, e.g. triethylamine.

The compounds of formula (XII) may be prepared by reacting a compound of formula (X) as previously defined or a salt thereof with a compound of formula (XIII).

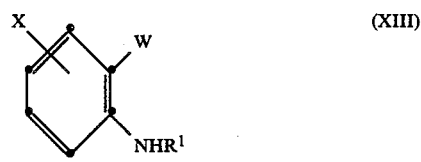

(wherein W, X and $R^1$ are as defined previously).

The reaction may conveniently be effected in an aqueous solvent such as water.

Alternatively the compounds of formula (XII) wherein $R^1$ represents other than hydrogen may be prepared by alkylating a compound of formula (XII) wherein $R^1$ represents a hydrogen atom with a compound of formula $R^a Z^a$ (where $R^a$ and $Z^a$ are as previously defined) in an analogous manner to process (C) above.

It should be appreciated that in some of the above transformations it may be necessary or desirable to protect any sensitive groups in the compound to avoid undesirable side reactions. The protecting groups used in the preparation of compounds of formula (I) are desirably groups which may be readily split off at a suitable stage in the reaction sequence, conveniently at the last stage. For example, during any of the reaction sequences described above, it may be necessary to protect the keto group. The carbonyl protecting group may be a conventional carbonyl protecting group such as those described in "Protective Groups in Organic Chemistry" Ed. J. F. W. McUmie (Plenum Press 1973) or "Protective Groups in Organic Synthesis" by Theodora W. Greene (John Wiley and Sons 1981). Thus for example, it may be a ketal such as a dialkyl or cyclic ketal, formed with an appropriate alkylorthoformate or diol, a thioketal, a bisulphite addition complex or an enol ether.

Compounds of general formula (I) may thus be prepared according to another general process (F), which comprises removal of any protecting groups from a protected form of a compound of formula (I). Deprotection may be effected using conventional techniques such as those described in 'Protective Groups in Organic Chemistry' Ed. J. F. W. McOmie (Plenum Press, 1973). Thus, a ketal such as an alkyleneketal group may be removed by treatment with a mineral acid such as hydrochloric acid. A thioketal group may be cleaved by treatment with a mercuric salt, e.g. mercuric chloride, in a suitable solvent, such as ethanol. An enol ether may be hydrolysed in the presence of an aqueous acid e.g. dilute sulphuric or hydrochloric acid.

The compounds of formula (I) may be converted into their physiologically acceptable salts according to conventional methods. Thus, for example, the free base of general formula (I) may be treated with an appropriate acid, preferably with an equivalent amount in a suitable solvent (e.g. aqueous ethanol).

Physiologically acceptable equivalents of a compound of formula (I) may be prepared according to conventional methods. Thus for example the free base of general formula (I) may be treated with an appropriate acid, preferably with an equivalent amount, in a suitable solvent.

Individual enantiomers of the compounds of the invention may be obtained by resolution of a mixture of enantiomers (e.g a racemic mixture) using conventional means, such as an optically active resolving acid; see for example 'Stereochemistry of Carbon Compounds' by E. L. Eliel (McGraw Hill 1962) and 'Tables of Resolving Agents' by S. H. Wilen.

Examples of optically active resolving acids that may be used to form salts with the racemic compounds include the (R) and (S) forms of organic carboxylic and sulphonic acids such as tartaric acid, di-p-toluoyltartaric acid, lactic acid and camphorsulphonic acid. The resulting mixture of isomeric salts may be separated, for example, by fractional crystallisation, into the diastereoisomers and if desired, the required optically active isomer may be converted into the free base.

The methods indicated above for preparing the compounds of the invention can be used as the last main step in the preparative sequence. The same general methods can be used for the introduction of the desired groups at an intermediate stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The following Preparations and Examples illustrate the invention. All temperatures are in °C.

Chromatography was carried out either in the conventional manner using silica gel (Merck, Kieselgel 60, Art. 7734 or 7747) or by flash chromatgraphy (W. C. Still, M. Kahn and A. Mitra, J. Org. Chem. 1978, 43, 2933) on silica (Merck 9385) and thin layer chromatography (t.l.c.) on silica (Macherly-Nagel, Polygram) except where otherwise stated. The following abbreviations define the eluent used for chromatography and t.l.c.:

| (A) | Ethyl acetate-hexane | 1:1 |
|---|---|---|
| (B) | Ethyl acetate-hexane | 4:1 |
| (C) | Dichloromethane-ethanol-0.88 ammonia | 91:8:1 |
| (D) | Dichloromethane-ethanol-0.88 ammonia | 89:10:1 |
| (E) | Dichloromethane-ethanol-0.88 ammonia | 100:8:1 |
| (F) | Dichloromethane-methanol | 19:1 |
| (G) | Dichloromethane-ethanol-0.88 ammonia | 150:8:1 |
| (H) | Dichloromethane-ethanol-0.88 ammonia | 75:8:1 |
| (I) | Dichloromethane-ethanol-0.88 ammonia | 970:30:3 |
| (J) | Dichloromethane-ethanol-0.88 ammonia | 945:50:5 |
| (K) | Dichloromethane-ethanol-0.88 ammonia | 100:10:1 |
| (L) | Ethyl acetate-methanol-triethylamine | 80:20:1 |

Intermediates were checked for purity by t.l.c. employing u.v. light for detection and spray reagents such as a solution of iodoplatinic acid (i.p.a.).

Proton ($^1$H) nuclear magnetic resonance (n.m.r.) spectra were obtained at 250 MHz using a Bruker AM or WM 250 instrument.

In the $^1$H n.m.r. data, the positions of the protons are numbered with reference to the following formula:

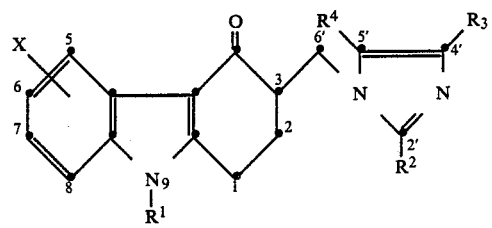

EXAMPLE 1

6-Fluoro-1,2,3,9-tetrahydro-9-methyl-3-[(2-methyl-1H-imidazol-1-yl) methyl]-4H-carbazol-4-one hydrochloride (i)

3-Hydroxy-2-cyclohexen-1-one (4-fluorophenyl)hydrazone

A suspension of 4-fluorophenylhydrazine hydrochloride (50 g) in water (500 ml) was treated with sodium hydroxide (12.3 g) in water (50 ml) and the resultant solution added to solution of cyclohexane-1,3-dione (97%, 35.6 g) in water (300 ml) over 2 h under nitrogen with stirring. After a further 30 min, the precipitate was filtered off, washed with water (50 ml), air dried for 1 h, and dried in vacuo over phosphorus pentoxide at 75° to give the title compound as a powder (65.3 g) m.p. 175°-176°.

(ii)

6-Fluoro-1,2,3,9-tetrahydro-4H-carbazol-4-one

Zinc chloride (powdered, freshly fused, 30.4 g) in ethyl acetate (35 ml) was refluxed at 100° with stirring until dissolution occured and then a portion (5 ml) of the ethyl acetate was distilled off. The product of Stage (i) (6.2 g) was added and refluxing at 100°-110° continued for 5 h. Zinc chloride (powered, freshly fused, 29.0 g) was added and heating continued for 16 h. The mixture was poured into water (250ml) and the stirred mixture heated at 50°-60° for 30 min. The mixture was extracted with ethyl acetate (4×150 ml) and the combined, dried ($Na_2SO_4$) extracts were evaporated onto silica gel (Merck 7734, 13 g) which was applied as a plug to a flash column of silica gel. Elution (A then B) afforded a solid (3.16 g) which crystallised from ethanol to give the title compound (1.92 g) m.p. 255°-260°.

(iii)

6-Fluoro-1,2,3,9-tetrahydro-9-methyl-4H-carbazol-4-one

The product of Stage (ii) (7.28 g), potassium carbonate (9.90 g), acetone (70 ml), and dimethylsulphate (5.1 ml) were vigorously stirred at room temperature overnight under nitrogen. The mixture was concentrated to one half of its volume and then stirred with water (350 ml) for 30 min. The mixture was filtered off, washed with water (50 ml), air-dried for 1 h, and dried in vacuo over phosphorus pentoxide to give the title compound as needles (7.59 g), m.p. 157.5°-158.5°.

(iv)

3-[(Dimethylamino)methyl]-6-fluoro-1,2,3,9-tetrahydro-9-methyl-4H-carbazol-4-one hydrochloride A solution of the product of Stage (iii) (6.72 g) in ethanol (150 ml) was heated at reflux under nitrogen with stirring and a mixture of paraformaldehyde (9.28 g) and dimethylamine hydrochloride (25.0 g) was added in ten equal portions over four days. The cooled reaction mixture was evaporated, aqueous 2M hydrochloric acid (150 ml) was added, and the mixture extracted with ethyl acetate (2×150 ml). The organic extracts were discarded and the aqueous phase was adjusted to pH 10 by the addition of aqueous 2M sodium carbonate. The mixture was extracted with ethyl acetate (3×150 ml), and the combined, dried ($Na_2SO_4$) extracts were evaporated to give a powder (6.08 g) m.p. 137°-139°. A portion of this material (0.78 g) in hot ethanol (10 ml) was treated with ethanolic hydrogen chloride, followed by hot ethyl acetate (70 ml) and when cool, with ether (150 ml). The precipitate was collected to give the title compound as crystals (0.68 g), m.p. 215°-217°.

(v)

6-Fluoro-1,2,3,9-tetrahydro-9-methyl-3[(2-methyl]-1H-imidazol-1-yl)methyl]-4H-carbazol-4-one hydrochloride The product of Stage (iv) (1.50 g) as the free base in DMF (25 ml) was treated with iodomethane (0.37 ml) at room temperature under nitrogen with stirring. After 10 min, 2-methylimidazole (2.24 g) was added, and the solution heated at 100° for 4 h. The reaction mixture was cooled, evaporated and the residue treated with aqueous saturated bicarbonate (50 ml) and ethyl acetate (100 ml). The resultant mixture was filtered and the solid dried in vacuo over phosphorus pentoxide. The filtrate was separated and the aqueous phase was further extracted with ethyl acetate (2×100 ml). The dried ($Na_2SO_4$) organic layers were evaporated, and the residue combined with the above solid and adsorbed from ethanol onto silica gel (Merck 7734, 1.0 g) which was applied as a plug to a flash column. Elution (C) afforded a solid, which was crystallised from ethanol then dissolved in hot ethanol (30 ml), treated with ethanolic hydrogen chloride and when cool, with dry ether (200 ml). The precipitate (638 mg) was collected and twice crystallised from ethanol-ethyl acetate to give the title compound as crystals (195 mg) m.p. 229.5°-230.5° (with darkening).

Nmr. $\delta$(DMSO-$d_6$) includes 1.9-2.2($CH_2$-2); 2.64($CH_3$-2'); 2.9-3.3($CH_2$-1 and H-3); 3.78($CH_3$-9); 4.27 and 4.65($CH_2$-6'); 7.15(aromatic H-7); 7.5 and 7.62(H-4' and 5'); and 7.6-7.7 (aromatic H-5 and 8).

EXAMPLE 2

(i)

1,3-Cyclohexanedione mono(4-bromophenylhydrazone)

A solution of 4-bromophenylhydrazine hydrochloride (2.24 g) and 1,3-cyclohexanedione (1.23 g) in water (60 ml) was stirred at room temperature for 1 h, giving a precipitate. The solid title compound was filtered off and dried (1.63 g). t.l.c (D), Rf 0.35 On cooling a second crop was obtained (0.395 g)

(ii)

6-Bromo-1,2,3,9-tetrahydro-4H-carbazol-4-one

The product of Stage (i) (1.5 g) was heated under reflux with dry zinc chloride (16 g) in glacial acetic acid (75 ml) for 24 h. The mixture was cooled, poured into water (200 ml), and the resulting solid filtered off and dried (0.95 g). Purification by flash chromatography (E) gave the title compound as a solid (125 mg). T.l.c. (F), Rf 0.65

(iii)

6-Bromo-1,2,3,9-tetrahydro-9-methyl-4H-carbazol-4-one

The product of Stage (ii) (40 g) was added to a suspension of potassium carbonate (49.5 g) in acetone (450 ml) and then stirred at room temperature for 30 min. Dimethyl sulphate (27 ml) was added and stirring continued for 4 h. The resulting mixture was added to water (2 l) and stirred for 30 min. The precipitate was filtered off and dried in vacuo for 24 h at 40° C. to give a solid (40 g). A sample (1 g) was purified by column chromatography (E) to afford the title compound as a solid (0.5 g) m.p. 231°-232°.

(iv)

6-Bromo-3-[(dimethylamino)methyl]-1,2,3,9-tetrahydro-9-methyl-4H-carbazol-4-one, hydrochloride Paraformaldehyde (1.5 g) and dimethylamine hydrochloride (3.75 g) were added to a solution of the product of Stage (iii) (10 g) in acetic acid (70 ml) and then heated to reflux for 8 h. On cooling to ambient temperature the reaction mixture was poured into water (400 ml). The oil which separated out was triturated with ether (500 ml) to give a solid (9 g) which was partitioned between ethyl acetate (2×30 ml) and saturated aqueous sodium carbonate (100 ml). The organic phase was evaporated and the residue purified by flash chromatography (G) to give the pure free base as a solid (0.40 g). A sample (0.4 g) was dissolved in ethanol (10 ml), filtered, and ethereal HCl (6 ml) was added. On addition of dry ether (20 ml), the title compound crystallized as a solid (0.38 g) m.p. 219°–220°.

(v)

6-Bromo-1,2,3,9-tetrahydro-9-methyl-3-[(2-methyl-1H-imidazol-1-yl)methyl]-4H-carbazol-4-one, oxalate A solution of 2-methylimidazole (2.6 g) and the product of Stage (iv) (4.7 g) in dimethylformamide (60 ml) was heated to 100° for 14 h. The resulting solution was poured into water (600 ml) and the precipitate was filtered off and dried in vacuo. Purification by flash chromatography (F) gave the pure free base as a solid (1.2 g). This was dissolved in hot ethanol (40 ml), filtered and added to a solution of oxalic acid (0.28 g) in hot ethanol (10 ml). On standing the title compound crystallised as a solid (1.2 g), m.p. 228°–229°.

Nmr δ(DMSO-$d_6$) includes 1.8–2.2($CH_2$-2); 2.52($CH_3$-2'); 2.9–3.($CH_2$-1 and H-3); 3.76($CH_3$-9); 4.23 and 4.58($CH_2$-6'); 7.20 and 7.47 (H-4' and 5'); and 7.42, 7.58 and 8.12 (aromatic H-7,8 and 5).

EXAMPLE 3

(i)

1,2,3,9-Tetrahydro-6-methoxy-4H-carbazol-4-one 1,3-Cyclohexanedione (8 g) was added to a solution of 4-methoxyphenylhydrazine hydrochloride (10 g) in ethanol (350 ml) and water (70 ml). The resulting solution was stirred at room temperature for 3 h and then at reflux for 14 h. On cooling to ambient temperature, the reaction mixture was poured into water (3 l) to give a solid, which was dried in vacuo to give the title compound, (6.0 g) m.p. 279°–279.5°.

(ii)

1,2,3,9-Tetrahydro-6-methoxy-9-methyl-4H-carbazol-4-one

Anhydrous potassium carbonate (2.24 g) was added to a solution of the product of Stage (i) (3 g) in acetone (30 ml) at room temperature and stirred for 30 min. Dimethyl sulphate (1.6 ml) was added and the mixture was heated to reflux for 4 h. The resulting solution was poured into water (150 ml) and the resulting precipitate filtered off to give the title compound as a solid (2.5 g), m.p. 150°–151°.

(iii)

3-[(Dimethylamino)methyl]-1,2,3,9-tetrahydro-6-methoxy-9-methyl-4H-carbazol-4-one hydrochloride A solution of the product of Stage (ii) (0.9 g) in ethanol (50 ml) containing paraformaldehyde (0.84 g) and dimethylamine hydrochloride (2.28 g) was refluxed for 2 days. The resulting solution was partitioned between water (250 ml) and dichloromethane (3×100 ml), the aqueous extracts were basified using aqueous sodium carbonate (30 ml) and extracted with dichloromethane (3×100 ml). The combined organic extracts were dried ($Na_2SO_4$) and concentrated in vacuo to give pure free base as a solid (0.37 g). The base (0.37 g) was dissolved in hot ethanol (10 ml) and ethereal hydrogen chloride (6 ml) added. On cooling the title compound crystallised as a solid (0.4 g) m.p. 152°–153°.

(iv)

1,2,3,9-Tetrahydro-9-methyl-3-[(2-methyl-1H-imidazol-1-yl)methyl]-6-methoxy-4H-carbazol-4-one, maleate 2-Methylimidazole (1.2 g) was added in three equal portions to a refluxing solution of the product of Stage (iii) (0.4 g) in dimethylformamide (25 ml) over a period of 3 days. The resulting solution was evaporated in vacuo and purified by "flash" chromatography (E) to give the free base (0.3 g). This was dissolved in hot ethanol (20 ml) and added to a solution of maleic acid (0.16g) in hot ethanol 10 ml. On cooling the title compound crystallised as a solid (0.21 g), m.p. 167.5°–168°.

Nmr δ(DMSO-$d_6$) includes 1.9–2.2($CH_2$-2); 2.62($CH_3$-2'); 2.9-3.2($CH_2$-1 and H-3); 3.73($CH_3$-9); 3.8($CH_3O$-6); 4.25 and 4.63($CH_2$-6'); 7.48 and 7.62(H-4' and 5'); and 6.89, 7.47 and 7.52 (aromatic H-7,8 and 5).

EXAMPLE 4

(i)

[4-(Phenylmethoxy)phenyl]hydrazine hydrochloride

A solution of sodium nitrite (16.1 g) in water was added dropwise over a period of ca 0.75 h to a cold (salt-ice bath) stirred suspension of 4-benzyloxyaniline hydrochloride (50 g) in concentrated hydrochloric acid (120 ml). The temperature was kept between −6° and −12° during the addition and stirring was continued for 1 h at the same temperature. The mixture was filtered (Hyflo) and the filtrate cooled to ca −18°. The solution of the diazonium salt was then added to a cold (−12°) stirred solution of tin (II) chloride dihydrate (157.9 g) in concentrated hydrochloric acid (400 ml) over a period of ca 0.5 h. During the addition the temperature gradually rose to 0°, and subsequently stirring was continued for 2 h while allowing the reaction mixture to reach room temperature. Filtration of the suspension afforded a solid. This material was washed with anhydrous ether (750 ml) and dried at room temperature for ca 16 h to present the title compound as a powder (34.4 g) m.p. 165°–170°. T.l.c. (E), Rf 0.5.

(ii)

1,2,3,9-Tetrahydro-6-(phenylmethoxy)-4H-carbazol-4-one 1,3-Cyclohexanedione (3.1 g) and the product of Stage (i) (5.6 g) in ethanol (196 ml) and water (39 ml) was stirred at room temperature for 3 h and then heated to reflux for 14 h. The resulting solution was allowed to cool, poured into water (500 ml) and the precipitate filtered and washed with isopropyl acetate and ether to give a solid. Recrystallisation from methanol gave the title compound as a solid (2.5 g) m.p. 235°–237°.

(iii)

3-[(Dimethylamino)methyl)]-1,2,3,9-tetrahydro-6-(phenyl-methoxy)-4H-carbazol-4-one hydrochloride Dimethylamine hydrochloride (10.1 g) and paraformaldehyde (4 g) were added in two equal portions over a period of 2 days to a solution of the product of Stage (ii) (2 g) in ethanol (100 ml) at reflux. The resulting solution was evaporated to dryness to give a solid (2 g). Purification by flash chromatography (E) gave the free base as a solid (1.4 g) which was dissolved in ethanol. Ethereal hydrochloric acid (6 ml) was added to give the title compound as a solid (1.4 g) m.p. 202°–203°.

(iv)

1,2,3,9-Tetrahydro-3-[(2-methyl-1H-imidazol-1-yl)methyl]-6-(phenylmethoxy)-4H-carbazol-4-one oxalate A solution of the product of Stage (iii) (2 g) in dimethylformamide (100 ml) was heated at 100° for 2 days with 2-methylimidazole (6.24 g). The resulting solution was evaporated to dryness and purified by flash chromatography (H) to give the free base as a solid (1.5 g). The base (0.20 g) was dissolved in hot ethanol (10 ml) and oxalic acid (0.047 g) in ethanol (5 ml) was added. On cooling the title compound crystallised as a solid (0.2 g) m.p. 168°–169°.

Analysis Found: C,64.8; H,5.0; N,8.7. $C_{24}H_{23}N_3O_2.C_2H_2O_4.0.5H_2O$ requires C,64.5; H,5.4; N,8.7%.

Nmr $\delta(DMSO-d_6)$ includes 1.8–2.1($CH_2$-2); 2.57 ($CH_3$-2'); 2.9–3.1 ($CH_2$-1 and H-3); 4.22 and 4.62 ($CH_2$-6'); 5.13 and 7.3–7.5($PbCH_2O$—); 7.47 and 7.51(H-4' and 5'); and 6.92, 7.40 and 7.57 (aromatic H-7,8 and 5).

EXAMPLE 5

1,2,3,9-Tetrahydro-6-hydroxy-3-[(2-methyl-1H-imidazol-1-yl)methyl]-4H-carbazol-4-one oxalate The product of Example 4 (iv) as the free base, (0.5 g) was hydrogenated at 70 psi over 10% palladium on charcoal (0.5 g of a 50% paste with water) in ethanol (50 ml) for 5 h. The catalyst was filtered off and the filtrate evaporated to dryness to give the pure free base as a solid (350 mg). To the free base (350 mg) in methanol (20 ml) was added oxalic acid (0.11 g) in ethanol (5 ml) and on cooling the title compound crystallised (250 mg) m.p. 162.5°–164° (foams).

Analysis found: C,57.7; H,5.0; N,11.00. $C_{17}H_{17}N_3O_2.C_2H_2O_4.O.5H_2O$ requires C,57.9; H,5.1; N,10.7%.

Nmr $\delta(DMSO-d_6)$ includes 1.8–2.1($CH_2$-2); 2.54($CH_3$-2'); 2.9–3.1($CH_2$-1 and H-3); 4.21 and 4.59($CH_2$-6'); 6.67, 7.22 and 7.38 (aromatic H-7, 5 and 8); and 7.28 and 7.46 (H-4' and 5').

EXAMPLE 6

1,2,3,9-Tetrahydro-9-methyl-3-[(2-methyl-1H-imidazol-1-yl)methyl]-6- (phenylmethoxy)-4H-carbazol-4-one oxalate Sodium hydride (0.045 g) was added to a solution of the product of Example 4 (iv) as the free base (0.5 g) in tetrahydrofuran (20 ml) and stirred at room temperature for 30 min. Iodomethane (0.08 ml) was added and stirring continued for 14 h. Water (1 ml) was added to the resulting solution which was then evaporated to dryness and purified by flash chromatography (E) to give pure free base as a solid (0.3 g). The free base (0.041 g) was dissolved in hot ethanol (10 ml) and oxalic acid (0.01 g) in ethanol (2 ml) was added. On cooling the title compound crystallised out as a solid (0.05 g) m.p. 198°–199°.

Analysis Found: C,65.6; H,5.7; N,8.5. $C_{25}H_{25}N_3O_2.C_2H_2O_4.0.2H_2O$ requires C,65.8; H,5.6; N,8.5%.

Nmr $\delta(DMSO-d_6)$ includes 1.8–2.2($CH_2$-2); 2.56($CH_3$-2'); 2.9–3.2($CH_2$-1 and H-3); 3.72($CH_3$-9); 4.22 and 4.59($CH_2$-6'); 5.15 and 7.3–7.5($PhCH_2O$—); 6.98, 7.40 and 7.62 (aromatic H-7, 8 and 5); and 7.33 and 7.48 (H-4' and 5').

EXAMPLE 7

1,2,3,9-Tetrahydro-6-hydroxy-9-methyl-3-[(2-methyl-1H-imidazol-1-yl)methyl]-4H-carbazol-4-one oxalate The product of Example 6, as the free base, (0.3 g) was hydrogenated at 70 psi for 14 h over 5% palladium oxide on charcoal (0.3 g of a 50% paste with water). The catalyst was filtered off, washed with methanol and the filtrate evaporated to dryness in vacuo, to give a solid (0.25 g). Purification by flash chromatography (E) gave pure free base as solid (0.19 g) which was dissolved in hot ethanol (30 ml). Oxalic acid (0.051 g) in ethanol (5 ml) was added and on cooling the title compound crystallised (0.24 g) m.p. 191.5°–192°.

Analysis Found: C,57.5; H,5.5; N,10.5. $C_{18}H_{19}N_3O_2.C_2H_2O_4.H_2O$ requires C,57.6; H,5.6; N,10.1%.

Nmr $\delta(DMSO-d_6)$ includes 1.8–2.2($CH_2$-2); 2.67($CH_2$-2'); 2.8–3.2($CH_2$-1 and H-3); 3.68($CH_3$-9); 4.22 and 4.60($CH_2$-6'); 6.73, 7.34 and 7.44 (aromatic H-7, 8 and 5); and 7.34 and 7.52 (H-4' and 5').

EXAMPLE 8

(i)

6-[(Dimethylamino)methyl]-3-methoxy-2-cyclohexen-1-one maleate n-Butyllithium (1.55M in hexane, 32.3 ml) was added to a stirred solution of dry diisopropylamine (7.0 ml) in dry tetrahydrofuran (60 ml) at −70° under nitrogen, and stirring was continued for 10 min. A solution of 3-methoxy-2-cyclohexen-1-one (5.0 g) in dry THF (10 ml) was added dropwise over 10 min, and stirring was continued at −70° to −60° for 40 min. The mixture was transferred by a double ended needle to a second flask containing a stirred suspension of N,N-dimethylmethylene ammonium iodide (Eschenmoser's salt) (13.9 g) in dry THF (40 ml) at −60°, and the mixture was allowed to warm to 0° with stirring over 4 h, and allowed to stand at room temperature overnight. The mixture was poured into 8% aqueous sodium bicarbonate (200 ml), further basified with 2N sodium hydroxide (100 ml), saturated with sodium chloride, and extracted with ether (4×200 ml). The organic layers were washed with brine, dried (MgSO₄) and evaporated to give an oil (7.65 g). Purification by short path chromatography (A) gave the free base as an oil (3.94 g). A portion of the oil (187 mg) was dissolved in methanol (1 ml), maleic acid (124 mg) in methanol (1 ml) was added and the solution was diluted with dry ether (70 ml) giving a precipitate which was filtered off, washed with ether and dried (in vacuo at room temperature) to present the title compound as a solid (283 mg), m.p. 132°–134°.

(ii)

3-Methoxy-6-[(2-methyl-1H-imidazol-1-yl)methyl]-2-cyclohexen-1-one maleate

Iodomethane (1.27 ml) was added to a stirred solution of the product of Stage (i) as the base (3.7 g) in dry, N,N-dimethylformamide (80 ml) at room temperature under nitrogen, and stirring was continued at room temperature for 25 min. 2-Methylimidazole (8.4 g) was added, and the mixture was heated at 80° for 4 h. The mixture was poured into brine (250 ml) and extracted with ethyl acetate (3×250 ml). The organic layers were washed with brine (3×250 ml) and the combined aqueous layers further extracted with ethyl acetate (3×400 ml). The combined organic layers were dried (MgSO$_4$) and evaporated to give a semi-solid (10.5 g). Purification by flash chromatography (A) gave the product as an oil which slowly crystallised (3.60 g). A sample (165 mg) was dissolved in methanol (0.5 ml), and maleic acid (91 mg) was added. Addition of dry ether (25 ml) gave a precipitate which was filtered off, washed with dry ether and dried (in vacuo at room temperature) to present the title compound as a solid (192 mg), m.p. 134.5°–135.5°.

(iii)

1,2,3,9-Tetrahydro-6-methyl-3-[(2-methyl-1H-imidazol-1-yl) methyl]-4H-carbazol-4-one maleate The product of Stage (ii) as the free base (1.0 g) was dissolved in water (30 ml), 2N hydrochloric acid (5 ml) was added and the mixture stirred at room temperature under nitrogen for 18 h.

4-Methylphenylhydrazine (3.6 g) was added and the mixture stirred at room temperature under nitrogen for 68 h. The resulting solution was poured into 8% aqueous sodium bicarbonate (30 ml), extracted with ethyl acetate (3×50 ml) and the combined, dried (MgSO$_4$) organic extracts evaporated to give a an oil. This was purified by short-path chromatography (I) to give a solid (300 mg) which was crystallised from methanol (10 ml) to give the free base as a solid (75 mg). A second crop (135F mg) was obtained by evaporation of the mother liquors and purification of the residue by short path chromatography (I and J). This was combined with a portion (40 mg) of the first crop, dissolved in hot ethanol (40 ml) and maleic acid (80 mg) in warm ethanol (5 ml) was added. The solution was evaporated and the residual solid crystallised from ethanol (5 ml) to give the title compound as crystals (130 mg), m.p. 162°–4°.

Nmr δ(DMSO-d$_6$) includes 1.9–2.2(CH$_2$-2); 2.40(CH$_3$-6); 2.62(CH$_3$-2'); 3.0–3.2(CH$_2$-1 and H-3); 4.27 and 4.63(CH$_2$-6'); 7.03, 7.31 and 7.78 (aromatic H-7,8 and 5) and 7.51 and 7.62 (H-4' and 5').

EXAMPLE 9

(i)

(3-methoxyphenyl)hydrazine hydrochloride

A suspension of 3-methoxyaniline (10 g) in concentrated hydrochloric acid (85 ml) was stirred at ca. 0° and a solution of sodium nitrite (5.75 g) in water (25 ml) was slowly added over a period of 30 min keeping the temperature of the mixture at ca. 0°. After 1 h a solution of tin II chloride dihydrate (59 g) in concentrated hydrochloric acid (50 ml) was added over a period of 1.5 h, to the cooled suspension keeping the temperature below 0° C. The suspension was stirred for a further 30 min, filtered and washed with dried ether to give the title compound as a solid (14 g) m.p. 171°.

(ii)

4-[(2-Methyl-1H-imidazol-1-yl)methyl]-1,3-cyclohexanedione-1-[(3-methoxyphenyl) hydrazone]

A solution of the product of Example 8(ii), as the free base (200 mg) in water (6 ml) and 2N hydrochloric acid (1 ml) was stirred for 3 h at room temperature. The product of Stage (i) (470 mg) was added and stirring continued for 14 h. The resulting solution was partitioned between ethyl acetate (4×40 ml) and sodium bicarbonate (30 ml). The combined organic layers were washed with brine (70 ml), dried (MgSO$_4$) and evaporated to give an oil (300 mg). Purification by flash chromatography (H) gave the title compound as a gum (180 mg). T.l.c. (H), Rf 0.5.

(iii)

1,2,3,9-Tetrahydro-7-methoxy-3-[(2-methyl-1H-imidazol-1-yl)methyl]-4H-carbazol-4-one The product of Stage (ii) (0.18 g) was heated to reflux in glacial acetic acid (5 ml) with zinc II chloride (1.8 g) for 5 h. The resulting solution was partitioned between sodium carbonate (50 ml) and ethyl acetate (4×40 ml). The combined organic layers were dried (MgSO$_4$) and evaporated to give an oil which was purified by flash chromatography (E) to give the title compound as a solid (0.08 g). T.l.c. (H), Rf 0.3

N.m.r. δ(DMSO)-d$_6$ includes 1.7–2.1(m, H-2); 2.33(s, —OCH$_3$); 2.8–3.0(m, H-1 and H-3); 4.07 and 4.57 (dd and dd, H-6'); 6.75 and 7.08 (s and s, H-4' and H-5'); 6.82(dd, H-6); 6.92(d, H-8) and 7.86(d, H-5).

EXAMPLE 10

1,2,3,9-Tetrahydro-7-hydroxy-3-[(2-methyl-1H-imidazol-1-yl)methyl]-4H-carbazol-4-one Boron tribromide (1.45 ml, 1M in CH$_2$Cl$_2$) was added dropwise to a cold (0°), stirred solution of the product of Example 9 (150 mg) in dry dichloromethane (12 ml) under nitrogen. Boron tribromide (0.725 ml) was added at 2×24 h intervals and stirring continued for a further 24 h. Methanol (10 ml) was added and the solution evaporated to dryness. The residue (270 mg) was purified by flash chromatography (K) to give the title compound as a powder (85 mg) m.p. 220°.

Nmr δ(DMSO-d$_6$) includes 1.7–2.1(CH$_2$-2); 2.33(CH$_3$-2'); 2.8–3.0(CH$_2$-1 and H-3); 4.07 and 4.47(CH$_2$-6'); 6.76 and 7.08(H-4'and 5') and 6.68, 6.78 and 7.76 (aromatic H-6,8 and 5).

EXAMPLE 11

(i)

6-(Dimethylamino)-1,2,3,9-tetrahydro-9-methyl-4H-carbazol-4-one

A mixture of the product of Example 2(iii) (2.78 g) copper powder (130 mg), cuprous chloride (112 mg) and aqueous dimethylamine (40% w/w, 40 ml) inside a glass insert was heated in a Roth autoclave at 196° for 8.5 h. The mixture was cooled to 20°, diluted with ethanol (150 ml) and filtered. The filtrate was concentrated in vacuo to leave a solid (3 g) which was purified by flash chromatography eluting with ethyl acetate. The resulting solid was triturated with ethyl acetate (3 ml) to give the title compound (0.47 g) as a solid m.p. 145°–147°.

(ii)

6-(Dimethylamino)-3-[(dimethylamino)methyl]-1,2,3,9-tetrahydro-9-methyl-4H-carbazol-4-one A solution of lithium diisopropylamide was prepared by adding n-butyllithium (nominally 1.5M in hexane, 1.36 ml) to a solution of di-isopropylamine (0.28 ml) in dry tetrahydrofuran (15 ml) under nitrogen. This solution was added dropwise to a stirred suspension of the product of Stage (i) (0.45 g) in dry tetrahydrofuran (20 ml) at −70° under nitrogen. After 1.75 h at −70° this solution was added dropwise via a double ended needle to a stirred suspension of N,N-dimethylmethyleneammonium iodide (Eschenmoser's salt, 0.66 g) in dry tetrahydrofuran (10 ml) at −70° under nitrogen. The mixture was allowed to warm to room temperature gradually (ca 2 h) and then stirred at room temperature for 18 h. The reaction mixture was evaporated in vacuo and the oily residue was partitioned between saturated potassium carbonate (60 ml) and ethyl acetate:ethanol (20:1, 2×75 ml). The combined organic layers were dried (Na$_2$SO$_4$) and evaporated in vacuo to leave a solid (ca 0.65 g) which was purified by flash chromatography (L) to give the title compound as a solid (0.17 g). T. l. c. (E), RF 0.16.

(iii)

6-(Dimethylamino)-1,2,3,9-tetrahydro-9-methyl-3-[(2-methyl-1H-imidazol-1-yl)methyl]-4H-carbazol-4-one maleate A solution of the product of Stage (ii) (100 mg) and 2-methylimidazole (30 mg) in dry dimethylformamide (6 ml) was heated at 100°-120° under nitrogen for 6 h. The mixture was evaporated in vacuo and the residue was purified by flash chromatography (L) collecting 20 ml fractions. Fractions 9-12 were combined and evaporated to leave a gum (0.04 g) This was combined with the residue from evaporation of fractions 13-23 (which contained 2-methyl-imidazole) diluted with water (20 ml) and ethanol (5 ml), heated on a steam bath for 2.5 h and evaporated in vacuo to leave a gum. Fractions 27-36 were combined and evaporated to give the free base of the title compound (0.03 g) as a solid, which was combined with the gum and purified by flash chromatography (L) to give a solid (0.06 g). This was triturated with a mixture of absolute ethanol (2 ml) and diethyl ether (5 ml) to leave a solid (0.04 g) which was dissolved in hot ethanol (3 ml) and treated with hot solution of maleic acid (14 mg) in ethanol (1 ml). The resulting solution was cooled (2° C.) and diluted with dry diethyl ether (15 ml) to precipitate the title compound (0.035 g) as a solid m.p. 148°-50°.

Nmr δ(CDCl$_3$) includes 1.8-2.4(CH$_2$-2); 2.81(CH$_3$-2′); 2.9-3.1(CH$_2$-1 and H-3); 3.05 (—N(CH$_3$)$_2$); 3.68(CH$_3$-9); 4.46 and 4.58(CH$_2$-6′); 7.23 and 7.28 (H-4′ and 5′); 7.02, 7.25 and 7.67 (aromatic H-7,8 and 5).

EXAMPLE 12

(i)

2,3,4,9-Tetrahydro-9-methyl-4-oxo-1H-carbazole-6-carbonitrile

A mixture of the product of Example 2(iii) (8.4 g) and copper (II) cyanide (8.5 g) in 1,3-dimethyl-3,4,5,6-tetrahydro-2(1H)-pyrimidone (90 ml) was stirred at 220°-230° under nitrogen for 1 h. The resulting solution was poured onto a mixture of ice (ca. 250 g) and a solution of ferric chloride (20 g) in water (20 ml). The mixture was allowed to warm to room temperature, stirred at 20° for 1.5 h and filtered to give a solid (ca. 15 g) which was dried in vacuo and continuously extracted with chloroform (500 ml) for 4 h and then with chloroform (500 ml) for 16 h. The first extract on evaporation gave the title compound (2.3 g) as a solid m.p. 190°-192°.

(ii)

2,3,4,9-Tetrahydro-9-methyl-4-oxo-1H-carbazole-6-carboxamide

A solution of the product of Stage (i) cyanonitrile (2.7 g) in concentrated sulphuric acid (30 ml) was heated at 80° for 1 h. The mixture was poured onto ice (ca. 500 g) to precipitate a solid which was filtered, washed with water (3×50 ml) and dried in vacuo to leave a solid (3.1 g). This was extracted with boiling absolute ethanol (1.5 l), the extract was evaporated to ca 2 ml, diluted with a mixture of chloroform:methanol (1:1, ca 20 ml) and filtered to give the title compound (0.53 g) as a solid m.p. 295°-298°.

(iii)

3-[(Dimethylamino)methyl]-2,3,4,9-tetrahydro-9-methyl-4-oxo-1H-carbazole-6-carboxamide A mixture of the product of Stage (ii) (1.8 g), paraformaldehyde (0.3 g) and dimethylamine hydrochloride (0.75 g) in acetic acid (14 ml) was heated at 80°-100° under nitrogen for 2 h. The reaction mixture was cooled (20°), evaporated in vacuo and purified by flash chromatography (L) to give a foam. A sample (0.2 g) was stirred in 0.88 ammonia 10 ml) for 3 days to precipitate to title compound (100 mg) as a solid. m.p. 171°-173° (foams).

(iv)

2,3,4,9-Tetrahydro-9-methyl-3-[(2-methyl-1H-imidazol-1-yl) methyl]-4-oxo-1H-carbazole-6-carboxamide maleate A solution of the product of Stage (iii) (0.33 g) and 2-methyl imidazole (0.1 g) in dry dimethylformamide (6 ml) was heated at 100° under nitrogen for 18 h. The reaction mixture was then dissolved in 2M hydrochloric acid (30 ml) and washed with ethyl acetate (3×30 ml). The acidic aqueous layer was basified (pH9) with potassium carbonate and extracted with a mixture of ethyl acetate:ethanol (10:3, 3×50 ml). The organic extracts were combined, washed with brine (3×50 ml), dried (Na$_2$SO$_4$) and evaporated to leave a gum (0.3 g) which was purified by column chromatography (L) to give a gum. Trituration with isopropanol (10 ml) gave a solid (0.11 g) which was dissolved in hot absolute ethanol (15 ml) and treated with a hot solution of maleic acid (38 mg) in ethanol (5 ml). The resulting solution was cooled (20°) and concentrated in vacuo to precipitate the title compound (0.069 g) as a solid. m.p. 185°-195° (foams).

Assay found : C,58.2; H,5.4; N,11.6. C$_{19}$H$_{20}$N$_4$O$_2$.C$_4$H$_4$.0.88H$_2$O requires : C,59.0; H,5.5; N,11.9%

The following examples illustrate pharmaceutical formulations according to the invention.

TABLETS FOR ORAL ADMINISTRATION

Tablets may be prepared by the normal methods such as direct compression of wet granulation.

The tablets may be film coated with suitable film forming materials, such as hydroxypropyl methylcellulose, using standard techniques. Alternatively the tablets may be sugar coated.

| Tablet | mg/tablet |
| --- | --- |
| Active Ingredient | 8.0 |
| Lactose NF* | 89.5 |
| Croscarmellose Sodium NF | 2.0 |
| Magnesium Stearate BP | 0.5 |
| Compression weight | 100.0 |

*of a grade suitable for direct compression.

The active ingredient is passed through a 60 mesh sieve, blended with the lactose, croscarmellose sodium and magnesium stearate. The resultant mix is compressed into tablets using 5.5 mm diameter punches.

Tablets of other strengths may be prepared by altering the ratio of active ingredient to lactose or the compression weight and using punches to suit.

FORMULATION FOR INJECTION

|  | mg/ml |
|---|---|
| Active Ingredient | 2.0 |
| Sodium Chloride BP | as required |
| Water for injection BP to | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. A compound of formula (I):

(I)

wherein $R^1$ represents a hydrogen atom or a $C_{1-10}$ alkyl, $C_{3-7}$ cycloalkyl, $C_{3-7}$cycloalkyl-$(C_{1-4})$-alkyl, $C_{3-6}$ alkenyl, $C_{3-10}$ alkynyl, phenyl or phenyl-$(C_{1-3})$alkyl group; one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-$(C_{1-3})$alkyl group and each of the other two groups, which may be the same or different, represents a hydrogen atom or a $C_{1-6}$ alkyl group; and X represents a halogen atom or a hydroxy, $C_{1-4}$ alkoxy, phenyl-$(C_{1-3})$-alkoxy or $C_{1-6}$ alkyl group or a group $NR^5R^6$ or $CONR^5R^6$ wherein $R^5$ and $R^6$, which may be the same or different, each represents a hydrogen atom or a $C_{1-4}$ alkyl or $C_{3-4}$ alkenyl group, or together with the nitrogen atom to which they are attached form a saturated 5 to 7 membered ring; and physiologically acceptable salts and solvates thereof.

2. A compound as claimed in claim 1, in which $R^1$ represents a hydrogen atom or a $C_{1-10}$ alkyl, $C_{3-7}$ cycloalkyl, $C_{3-6}$ alkenyl, phenyl or phenyl-$(C_{1-3})$alkyl group; and X represents a halogen atom, or a hydroxy, $C_{1-4}$ alkoxy or $C_{1-6}$ alkyl group, or a group $NR^5R^6$ or $CONR^5R^6$.

3. A compound as claimed in claim 1, in which X represents a halogen atom, a $C_{1-6}$ alkyl group, or a hydroxy group.

4. A compound as claimed in claim 1 in which the substituent X is at the 6-position of the tetrahydrocabazolone ring.

5. A compound as claimed in claim 1, in which $R^1$ represents a hydrogen atom or a $C_{1-6}$ alkyl, $C_{3-7}$ cycloalkyl or $C_{3-6}$ alkenyl group.

6. A compound as claimed in claim 1, in which one of the groups $R^2$, $R^3$ and $R^4$ represents a $C_{1-3}$ alkyl, $C_{3-6}$ cycloalkyl or $C_{3-6}$ alkenyl group and each of the other two groups, which may be the same or different, represents a hydrogen atom or a $C_{1-3}$ alkyl group.

7. A compound as claimed in claim 1 in which $R^2$ represents a hydrogen atom and one of the groups $R^3$ and $R^4$ represents a $C_{1-3}$alkyl group.

8. A compound as claimed in claim 1 in which $R^2$ represents a hydrogen atom and $R^3$ and $R^4$ both represent a $C_{1-3}$alkyl group.

9. A compound as claimed in claim 1 in which $R^2$ represents a $C_{1-3}$alkyl group and $R_3$ and $R_3$ both represent a hydrogen atom.

10. A compound selected from the group consisting of 6-fluoro-1,2,3,9-tetrahydro-9-methyl-3-[(2-methyl-1H-imidazol-1-yl) methyl]-4H-cabazol-4-one;

6-bromo-1,2,3,9-tetrahydro-9-methyl-3-[(2-methyl-1H-imidazol-1-yl)methyl]-4H-carbazol-4-one;

1,2,3,9-tetrahydro-6-hydroxy-3-[(2-methyl-1H-imidazol-1-yl)methyl]-4H-carbozol-4-one;

1,2,3,9-tetrahydro-6-hydroxy-9-methyl-3-[(2-methyl-1H-imidazol-1-yl)methyl]-4H-carbazol-4-one;

1,2,3,9-tetrahydro-6-methyl-3-[(2-methyl-1H-imidazol-1-yl)methyl]-4H-carbazol-4-one;

6-(dimethylamino)-1,2,3,9-tetrahydro-9-methyl-3-[(2-methyl-1H-imidazol-1-yl)methyl]-4H-carbazol-4-one and physiologically acceptable salts and solvates thereof.

11. A pharmaceutical composition for the treatment of a condition caused by disturbance of "neuronal" 5HT function comprising at least one compound of formula (I) as defined in claim 1 or a physiologically acceptable salt or solvate thereof in an amount effective to relieve said condition together with at least one physiologically acceptable carrier or excipient.

12. A method of treating a condition caused by disturbance of "neuronal" 5HT function which comprises administering to a patient an effective amount of a compound of formula (I) as defined in claim 1 or a physiologically acceptable salt or solvate thereof to relieve said condition.

13. A compound of Formula (VI)

(VI)

wherein $R^1$ represents a hydrogen atom or a $C_{1-10}$ alkyl, $C_{3-7}$ cycloalkyl, $C_{3-7}$cycloalkyl-$(C_{1-4})$-alkyl, $C_{3-6}$ alkenyl, $C_{3-10}$ alkynyl, phenyl or phenyl-$(C_{1-3})$alkyl group;

one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-$(C_{1-3})$alkyl group and each of the other two groups, which may be the same or different, represents a hydrogen atom or a $C_{1-6}$ alkyl group) and X represents a halogen atom or a hydroxy, $C_{1-4}$ alkoxy, phenyl-($C_{1-3}$)-alkoxy or $C_{1-6}$ alkyl group or a group $NR^5R^6$ or $CONR^5R^6$ wherein $R^5$ and $R^6$, which may be the same or different, each represents a hydrogen atom or a $C_{1-4}$ alkyl or $C_{3-4}$ alkenyl group, or together with the nitrogen atom to which they are attached form a saturated 5 to 7 membered ring; and A represents a hydrogen atom or a hydroxyl group.

* * * * *